(12) United States Patent
Dusemund et al.

(10) Patent No.: US 8,716,039 B2
(45) Date of Patent: May 6, 2014

(54) MONITORING APPARATUS AND METHOD FOR IN-SITU MEASUREMENT OF WAFER THICKNESSES FOR MONITORING THE THINNING OF SEMICONDUCTOR WAFERS AND THINNING APPARATUS COMPRISING A WET ETCHING APPARATUS AND A MONITORING APPARATUS

(75) Inventors: Claus Dusemund, Singapore (SG); Martin Schoenleber, Aschaffenburg (DE); Berthold Michelt, Wiesbaden (DE); Christoph Dietz, Obertshausen (DE)

(73) Assignee: Precitec Optronik GmbH, Neu-Isenburg (DE)

( * ) Notice: Subject to any disclaimer, the term of this patent is extended or adjusted under 35 U.S.C. 154(b) by 0 days.

(21) Appl. No.: 13/521,736

(22) PCT Filed: Jan. 10, 2011

(86) PCT No.: PCT/IB2011/050091
§ 371 (c)(1), (2), (4) Date: Jul. 11, 2012

(87) PCT Pub. No.: WO2011/086490
PCT Pub. Date: Jul. 21, 2011

(65) Prior Publication Data
US 2013/0034918 A1 Feb. 7, 2013

(30) Foreign Application Priority Data

Jan. 14, 2010 (DE) .................... 10 2010 000 079 U
Mar. 12, 2010 (DE) ......................... 10 2010 015 944

(51) Int. Cl.
*H01L 21/66* (2006.01)
*G01B 11/06* (2006.01)

(52) U.S. Cl.
USPC ............... 438/16; 257/E21.525; 257/E21.53; 356/479; 356/497

(58) Field of Classification Search
USPC ..................... 257/E21.53, E21.523, E21.525; 356/479, 497; 438/16
See application file for complete search history.

(56) References Cited

U.S. PATENT DOCUMENTS

| | | | | |
|---|---|---|---|---|
| 5,392,124 A | * | 2/1995 | Barbee et al. | 356/632 |
| 5,905,572 A | * | 5/1999 | Li | 356/479 |
| 6,672,943 B2 | * | 1/2004 | Vogtmann et al. | 451/41 |
| 6,673,654 B2 | * | 1/2004 | Ohno et al. | 438/118 |
| 6,897,964 B2 | | 5/2005 | Takahashi et al. | |
| 7,525,732 B2 | * | 4/2009 | Uehara et al. | 359/620 |
| 2003/0090671 A1 | | 5/2003 | Takahashi et al. | |
| 2006/0194419 A1 | * | 8/2006 | Araki | 438/489 |
| 2007/0231717 A1 | | 10/2007 | Rivers et al. | |
| 2007/0258095 A1 | | 11/2007 | Olivier et al. | |
| 2009/0257065 A1 | | 10/2009 | Li | |
| 2010/0051068 A1 | * | 3/2010 | Miyanari | 134/95.2 |

FOREIGN PATENT DOCUMENTS

| | | |
|---|---|---|
| DE | 102010000079 | 1/2010 |
| DE | 102010015944 | 7/2011 |
| EP | 0905476 | 3/1999 |
| WO | 2011086490 | 7/2011 |

OTHER PUBLICATIONS

Huang et al.; "Optical coherence tomography", Science, vol. 254, No. 5035, S. 1178-1181 (1991).
Vakhtin et al.; "Common-path interferometer for frequency-domain optical coherence tomography"; Applied Optics, vol. 42, No. 34, S. 6953-6957 (2003).
Dusemund; International Search Report and Written Opinion for serial No. PCT/IB2011/050091, filed Jan. 10, 2011, mailed Apr. 12, 2011, 3 pgs.
Dusemund; International Preliminary Report on Patentability for serial No. PCT/IB2011/050091, filed Jan. 10, 2011, mailed Aug. 16, 2012, 14 pgs.

* cited by examiner

*Primary Examiner* — John C Ingham

(74) *Attorney, Agent, or Firm* — Taylor English Duma LLP

(57) ABSTRACT

According to the invention, a monitoring device (12) is created for monitoring a thinning of at least one semiconductor wafer (4) in a wet etching unit (5), wherein the monitoring device (12) comprises a light source (14), which is designed to emit coherent light of a light wave band for which the semiconductor wafer (4) is optically transparent. The monitoring device (12) further comprises a measuring head (13), which is arranged contact-free with respect to a surface of the semiconductor wafer (4) to be etched, wherein the measuring head (13) is designed to irradiate the semiconductor wafer (4) with the coherent light of the light wave band and to receive radiation (16) reflected by the semiconductor wafer (4). Moreover, the monitoring device (12) comprises a spectrometer (17) and a beam splitter, via which the coherent light of the light wave band is directed to the measuring head (13) and the reflected radiation is directed to the spectrometer (17). The monitoring device (12) further comprises an evaluation unit (18), wherein the evaluation unit (18) is designed to determine a thickness $d(t)$ of the semiconductor wafer (4) from the radiation (16) reflected by the semiconductor wafer (4) during thinning of the semiconductor wafer (4) by means of a method that is selected from the group consisting of a 1D-se FDOCT method, a 1D-te FDOCT method and a 1D-se TDOCT method.

20 Claims, 2 Drawing Sheets

MONITORING APPARATUS AND METHOD FOR IN-SITU MEASUREMENT OF WAFER THICKNESSES FOR MONITORING THE THINNING OF SEMICONDUCTOR WAFERS AND THINNING APPARATUS COMPRISING A WET ETCHING APPARATUS AND A MONITORING APPARATUS

The invention relates to a monitoring apparatus and a method for the in-situ measurement of wafer thicknesses during the thinning of semiconductor wafers and a thinning apparatus with a monitoring apparatus. The thinning apparatus also has apparatus for thinning at least one semiconductor wafer comprising a control unit for controlling the application of an amount of etching or rinsing liquid and controlling the speed of a rotating retaining device on which the semiconductor wafer is positioned. In addition, the thinning apparatus has a measuring apparatus for measuring the thickness of the rotating semiconductor wafer comprising a contact-free measuring head and a light source with coherent light emission close to the infrared range.

A thickness measuring apparatus and corresponding thickness measuring method and a wet etching apparatus and wet etching process using the measuring apparatus and the measuring method are known from U.S. Pat. No. 6,897,964 B2. The known measuring apparatus as disclosed in this prior art is shown in FIG. 2 with a measuring apparatus 12 and an etching apparatus. The known etching apparatus has apparatus 5' for thinning at least one semiconductor wafer 4. This apparatus 5' is provided with a rotating retaining device 6 for the semiconductor wafer 4 to be thinned which is positioned supported by a substrate 32 on a rotating plate 21. The rotating plate 21 is driven by a motor 19 with a rotational speed n which is controlled by a control unit 11. Etching liquids 8 and/or rinsing liquids 9 are fed by a dispenser 7 to a nozzle 50 which wets the surface to be etched 10 of the semiconductor wafer to be thinned 4 with an etching film 22.

During the thinning of the semiconductor 4, a measuring apparatus 12' measures the thickness of the semiconductor wafer to be thinned 4 at time intervals using a measuring head 13 on the basis of the time difference between the component of the beam reflected on the surface 10 of the semiconductor wafer 4 to be etched and the component reflected by an opposing surface 48 of the semiconductor wafer 4 once it has passed through the semiconductor wafer. To this end sequentially coherent light in the near infrared range is directed from a light source 14 by light wave guides 24 and 26 to the measuring head 13 and onto the semiconductor wafer 4, there being positioned between the two light wave guides 24 and 26 an optical coupler 27 which feeds the light from the light source 14 both to the measuring head 13 and via an optical reference light wave guide 47 to a reference light generator 44.

This reference light generator 44 is crucial in this type of apparatus from the prior art in determining the difference in duration between the reflection of the two surfaces 10 and 48 of the semiconductor 4 periodically at intervals. To this end the reference light generator 44 has a mirror galvanometer 37 which cooperates with a pivoting parallel plate glass substrate 38 and using a reflector mirror 39 forms an optical reference path 46 which feeds the optical reference signal via a light wave guide 25 to a photo detector 45 via the optical reference light wave guide 47 and the optical coupler 27 while at the same time the mirror galvanometer 37 supplies the difference in duration between the two reflected beam components between the surface 10 and the surface 48 of the semiconductor wafer 4 to an evaluation unit 18 via an optical reference path detector 40. The evaluation unit 18 also receives the measuring signals from the photo detector 45 and periodically detects a raw thickness in a first signal processing circuit 41 in conjunction with a raw thickness calculation device 42 and makes a statistical thickness calculation 43 from the raw data on the basis of the broad spread of the raw thickness calculations in a further calculation block 43 of the evaluation unit 18.

Consequently, the known apparatus 2 for measuring wafer thicknesses during the thinning of semiconductor wafers 4 has the disadvantage that the thickness measurement depends on a mirror galvanometer 37 which does not permit continuous detection of wafer thickness 3 due to the pivoting movement of the glass substrate 38. Raw thickness can only be calculated sequentially at intervals. Furthermore, with this known apparatus 2 the spread of the calculated raw thicknesses is such that after a final number of raw thickness measurements it is necessary to carry out a statistical thickness calculation to determine the most probable thickness reduction curve.

Due to the need for a reference arm which has to be linked to the optical coupler 27 and is connected to the evaluation unit 18 to allocate the measurement values of the photo detector 45 to the two surfaces 10 and 48 of the semiconductor wafer 4, the resulting apparatus is vibration-sensitive due to the mirror galvanometer 37 and relatively unreliable due to the spread of the periodically determined raw thickness values. With this method, moreover, it is not possible to detect the reduction in wafer thickness 3 continuously during the thinning of the semiconductor wafer 4 since only a limited number of raw thickness values can be ascertained during one revolution of the semiconductor wafer 4 on the rotating retaining device 6.

The object of the invention is to create a new monitoring apparatus and a new method for measuring wafer thicknesses during the thinning of semiconductor wafers for monitoring the thinning of at least one semiconductor wafer and a thinning apparatus with a monitoring apparatus which overcome the disadvantages of the known apparatus and the known method and improve the robustness and reliability of thickness measurement during the thinning of semiconductor wafers.

This object is achieved by means of the subject matter of the independent claims. Advantageous developments of the invention are detailed in the dependent claims.

The invention discloses a monitoring apparatus for monitoring the thinning of at least one semiconductor wafer in a wet etching apparatus, the monitoring apparatus comprising a light source configured to emit coherent light in a light wave band to which the semiconductor wafer is optically transparent. In addition, the monitoring apparatus has a measuring head which is positioned contact-free in relation to a surface of the semiconductor wafer to be thinned, said measuring head being configured to irradiate the semiconductor wafer with the coherent light of the light wave band and receive a beam reflected by the semiconductor wafer. Furthermore, the monitoring apparatus comprises a spectrometer and a beam splitter by means of which the coherent light of the light wave band is directed to the measuring head and the reflected beam is directed to the spectrometer. In addition, the monitoring apparatus has an evaluation unit, said evaluation unit being configured to determine the thickness $d(t)$ of the semiconductor wafer from the beam reflected by the semiconductor wafer during the thinning of the semiconductor wafer by means of a method selected from a group consisting of a 1D-se FD-OCT (one dimensional spatially encoded Fourier Domain Optical Coherence Tomography) method, a 1D-te FD-OCT (one dimensional time encoded Fourier Domain Optical Coherence Tomography) method and a 1D-se TD-OCT (one dimensional spatially encoded Time Domain Optical Coherence Tomography) method.

This monitoring apparatus has the advantage that detecting wafer thickness is not dependent on a movable or pivotable reference light apparatus. Instead the monitoring apparatus has a static spectrometer in the case of the 1D-se FD-OCT and 1D-te FD-OCT methods and a static Fourier spectrometer in the case of the 1D-se TD-OCT method with which it is possible to calculate a spectrum by numerical Fourier transformation. These static macromechanical components permit evaluation in an evaluation unit in which the number per revolution of evaluated wafer thickness depends solely on the computing speed and capacity of the evaluation unit connected to the spectrometer. In addition, the monitoring apparatus has the advantage of requiring no reference arm.

Only the 1D-te FD-OCT method requires a time-adjustable laser which operates with a time-adjustable oscillating micromechanical device to adjust the laser as the light source. However, at 400 kHz the oscillation of the micromechanical apparatus and thus the measuring rate of is more than twice that observed with the known galvanometer.

In the Fourier transformation the light wave lengths reflected by the two surfaces of the semiconductor wafer are fanned out, inverted and continuously evaluated by Fourier analysis or Fourier transformation using an FD-OCT method. It is irrelevant whether the measuring head detects the wafer thickness from below, through a central opening for example, or whether the wafer thickness of the semiconductor wafer is monitored from above.

In a preferred embodiment relating to the 1D-se FD-OCT or 1D-te FD-OCT method the spectrometer has a diffraction grating, said diffraction grating being configured to fan out the spectral distribution of the reflected beam.

In a further embodiment of the invention, the measuring head is protected from the etching solutions by an optically transparent, in particular infrared-transparent, protective screen which preferably comprises sapphire. Sapphire is a monocrystalline aluminium oxide which cannot be attacked by a silicon etching solution. When the measuring head is used for other etching solutions for other semiconductor materials suitably adjusted protective screens or protective films must be provided.

In a further embodiment the evaluation unit is also configured to determine the thickness $d_f(t)$ and evenness of an etching film consisting of etching liquid.

In a further embodiment the beam splitter is an optical coupler. In addition, the monitoring apparatus may comprise at least one first light wave guide which connects the measuring head to the optical coupler, at least one second light wave guide which connects the optical coupler to the light source and at least one third light wave guide which connects the optical coupler to the spectrometer.

The invention also relates to a thinning apparatus comprising a wet etching apparatus and a monitoring apparatus according to one of the preceding embodiments.

The thinning apparatus has the advantages already detailed in reference to the monitoring apparatus. In order to avoid repetition they will not be reiterated here.

The wet etching apparatus preferably has at least one rotating retaining device for the semiconductor wafer to be thinned. In this arrangement the retaining device can be a rotary table driven by a speed-controlled motor.

In a further embodiment the thinning apparatus has a dispenser for an etching liquid for thinning the semiconductor wafer. The dispenser can have different nozzles such as a drip nozzle or a spray nozzle, the droplet nozzle producing droplets of liquid while the spray nozzle forms a mist of liquid. In one embodiment of the invention this nozzle of the dispenser is fixed centrally above the rotating semiconductor wafer to be thinned. Since the centre of the semiconductor wafer moves less than its edge regions and thus develops a lower centrifugal force for the etching film, erosion or reduction in thickness is less in the centre than at the edge of the semiconductor wafer if the etching apparatus is equipped for one semiconductor wafer only. Alternatively, the nozzle can pivot in order to even out the thinning process.

The thinning apparatus preferably has a coupling unit and a control/regulating unit as part of the wet etching apparatus, said coupling unit being connected to the evaluation unit and configured to stop the etching process when the thinned semiconductor wafer reaches a predetermined final thickness $d_z$. The coupling unit is preferably connected via signal lines to the evaluation unit and the control unit and can be integrated in the monitoring apparatus or the control unit. The coupling unit is preferably positioned several meters away from the measuring head and separate from the wet etching apparatus for thinning the semiconductor wafer and has a monitor with an appropriate display and user interface. The monitor may thus have a touch screen.

The latter embodiments have the advantage that they offer improved process control for the semiconductor wafer thinning method whilst at the same time preventing over-etching. The specification of the thickness tolerances can be limited to a few tens of nanometers when thinning semiconductor wafers. Even if the etching effect of the etching solution is dependent on ageing phenomena, the predetermined final thickness of the semiconductor wafer of a whole batch can be achieved with a large number of semiconductor wafers irrespective of such etching liquid ageing phenomena. The metering of the etching composition and the quantity of the etching solution to be supplied can be controlled/regulated using this thinning apparatus. Finally, it is possible to achieve a small final thickness of semiconductor wafers when thinning. A further advantage of this thinning apparatus is the lack of need for any preparatory process using so-called "dummy" wafers. It is also possible to reduce the number of process steps in the chemical/mechanical semiconductor wafer thinning process needed; intermediate steps for checking in particular can be omitted entirely.

The number of measuring points per semiconductor wafer revolution can be increased several fold dependent on the computing capacity and speed of the evaluation unit in comparison with the known scanning technique using a galvanometer reference such that the accuracy of the settable final thickness can be preset to ±70 nanometer per wafer. The new thinning apparatus achieves a high level of reproducibility of the pre-settable final thickness of the thinned semiconductor wafer independent of the state of the etching solution such that, for example, in a batch of one thousand wafers it is possible to achieve a wafer thickness spread of less than ±0.5 µm.

In a preferred invention the control unit has a regulator which is configured to regulate the quantity of etching liquid to be dispensed by the dispenser in accordance with the thickness $d_f(t)$ of the etching film consisting of etching liquid applied and/or in accordance with the reduction in thickness $\Delta d(t)$ of the semiconductor wafer.

In a further embodiment of the thinning apparatus it is configured for thinning silicon wafers. This means that the thinning apparatus, and preferably the wet etching apparatus, feeds an etching solution comprising fluoric acid and an oxidising agent such as nitric acid, dissolved peroxydisulfate or dissolved Ce(IV) salts to the dispenser which produces an etching film for the rotating silicon semiconductor wafer via a pivoting or fixed nozzle. This etching film is evened out by the rotation of the rotating retaining device and its etching effect is controlled by a buffer solution which may contain sulphuric acid and/or phosphoric acid. Moreover, the surface of the silicon wafer to be provided with the etching film should be wetted as evenly as possible by the etching film, to which end a liquid or liquefied wetting agent can be admixed to the etching solution.

This means that the dispenser in this embodiment cooperates with at least four acid containers which are connected to the control unit which controls the composition and quantity of the etching solution, the buffer solution and the wetting agent. In this arrangement, the mixing ratio of the acids can be adjusted to any reduction in thickness $\Delta d(t)$ measured by the measuring apparatus during the thinning of the semiconductor wafer. Also connected to the dispenser is a rinsing agent supply by means of which the control unit stops the etching process when the predetermined final thickness of the silicon wafer to be thinned is achieved.

In addition to the supply of appropriate etching and rising agents to the dispenser, the wave length range of the light source is also dependent on the type of semiconductor wafer, e.g. silicon wafer, to be thinned. A silicon wafer is not transparent to visible light and a white, visible light is not therefore a suitable light source. The light source provided for measuring the thickness of silicon wafers has a light wave band that lies at least partially above the absorption edge. In a preferred embodiment the light source has a light wave band of approx. 100 nanometers in the near infrared range between 1.25 µm and 1.35 µm or between 1.5 µm and 1.6 µm. It is also possible to measure semiconductor wafers which are transparent to visible light, such as GaAs and InP, using the monitoring apparatus during the thinning of the semiconductor wafer, but this requires alternative etching solutions, buffer solutions and wetting agents.

Semiconductor wafers not transparent to visible light made of GaInAs or InAs can be measured with the monitoring apparatus disclosed in the invention during the thinning of the semiconductor wafer using appropriately adjusted infrared light wave bands. In general, any semiconductor material, in particular semiconductor materials of III-V or II-VI compounds can be continuously monitored and measured during the thinning of a plurality of semiconductor wafers with the monitoring apparatus disclosed in the invention.

The thickness and evenness of the etching film can be controlled/regulated using the control unit by controlling the speed of the drive motor of the rotating retaining device. It is also possible by measuring with the monitoring apparatus to set an etching film thickness such that it can be regulated. To this end the control unit of the wet etching apparatus also has a regulating unit.

In an alternative configuration of thinning apparatus a plurality of semiconductor wafers is positioned in the edge region of a rotating table to even out the etching effect. In this case, too, the monitoring apparatus is able to continuously detect the thinning of a plurality of semiconductor wafers on one single rotating retaining device. With a thinning apparatus of this kind with a wet etching apparatus for thinning one or more semiconductor wafers the surfaces to which semiconductor structures have already been applied are positioned on the side of the semiconductor not exposed to the etching liquids and rinsing liquids opposite the surface to be etched.

A further possible method of evening out the etching film is to produce the etching film on the rotary table and to press the surface of the semiconductor wafer to be etched onto this etching film. Here the measuring head can be directed upwards from below onto the surface of the semiconductor wafer to be etched, through a central opening in the rotary table for example, to detect the wafer thickness while the semiconductor wafer is being thinned using this type of etching apparatus.

In one embodiment, the measuring head itself is connected to the evaluation unit via a multimode light wave guide. To this end the monitoring apparatus has an optical coupler which both directs the light from the light source to the measuring head and directs the beam reflected by the measurement object such as a semiconductor wafer to the spectrometer. There the spectrum of the reflected light is represented on a detector row. The spectrum read off is scaled up to the number of waves and Fourier transformed. The optical path lengths of the corresponding layers from the reflected spectrum are determined from the positions of the peaks occurring in the Fourier transformation in the FD-OCT method.

The measurement values recorded can be read off directly at the coupling unit which preferably has a two-line LC display or they can be displayed on the monitor of a central computer with a touch screen via which it is possible to enter the individual initial and boundary conditions such as the refraction index of the materials to be examined, the number of different layers, threshold values for reflection intensities, etc.

While the monitoring apparatus detects the optical lengths of individual layers, a measurement program with connected PC is able to determine and display on the monitor the layer thicknesses determined for the materials used for the thickness measurement. Function keys on the PC can be used instead of a touch screen. The high measurement rate of up to 4000 measurements per second and the relatively low measurement spot size in a two dimensional area of a few µm² (square micrometers) also permit localised layer thickness measurement. The monitoring apparatus can also be fitted with a multi-axis positioning system to show the planar distribution of the final thickness once the etching process is complete.

Since the measuring head operates with no movable or electronic components it is robust and can be connected via the Eight wave guide to a remote measuring apparatus, and to the electronic circuitry available in the measuring apparatus, several meters away such that the measuring apparatus can be operated separately from the measuring head.

Various measurement heads are available for various requirements, a preferred measuring head covering a measurement range for the thinning of semiconductor wafers of 2 to 250 µm with a resolution of 10 mm and a reproducibility of 20 nm at a refraction index of n=1. The working distance of the measuring head from the object to be thinned can be varied by several millimeters with no negative influence on the measurement result since it is the thickness of the semiconductor wafer or the thickness of the etching film which is measured continuously rather than the increase in distance between the measuring head and the object to be thinned. In addition to a resolution of 10 nm, the measuring head specified above also achieves an absolute accuracy of 70 nm.

The apparatus disclosed in the invention overcomes other common problems including those caused by shadow effects in triangulation and the high surface quality demanded for monochromatic and interferometer measurements. It can be used to measure both smooth and rough, highly reflective and transparent surfaces.

A method for monitoring the thinning of at least one optically transparent semiconductor wafer in a wet etching apparatus, said wet etching apparatus comprising at least one rotating retaining device, comprises the following steps. At least one semiconductor wafer is fixed on the rotating retaining device in the wet etching apparatus. In this method a continuous measuring process can be started by the activation of a light source and the emission from the light source of coherent light in the near-infrared range in a light wave band preferably several tens of nanometers wide with which a measuring head irradiates the rotating semiconductor wafer, reflected radiation being received by the measuring head, and by the activation of a spectrometer which receives the reflected beam. Simultaneously or subsequently an etching process for thinning the rotating semiconductor wafer can be started by the application of an etching solution by a dispenser, preferably also regulating the quantity of etching solution and the rotational speed of the semiconductor wafer by means of a control unit. In addition, the spectrometrically fanned out reflected beam is evaluated continuously to determine the thickness d(t) of the semiconductor wafer achieved during the thinning of the semiconductor wafer by means of a method selected from a group consisting of a 1D-se FD-OCT (one dimensional spatially encoded Fourier Domain Optical Coherence Tomography) method, a 1D-te FD-OCT (one dimensional time encoded Fourier Domain Optical Coherence Tomography) method and a 1D-se TD-OCT (one dimensional spatially encoded Time Domain Optical Coherence Tomography) method.

This method has the advantage over the method for thinning semiconductor wafers known from the prior art and disclosed in U.S. Pat. No. 6,897,964 B2 that there is no need for optical reference light generation or an optical reference path. Instead the wafer thickness of a semiconductor wafer to be thinned is continuously detected by spectral analysis of the reflected beam from both surfaces of the semiconductor wafer using a 1D-OCT method or by means of a Fourier transformation using an FD-OCT method.

Each boundary layer generates a reflected spectrum which due to the Fourier transformation results in a clear peak with which the optical lengths of the individual layers positioned a distance from the measuring head during thinning can be determined at a high scanning rate. As has already been mentioned several times, this scanning rate depends simply on the computing speed and capacity of the evaluation unit. Consequently, it is possible to reach thickness measurement rates of up to 4000 per second which simultaneously lead to high reproducibility of the values determined. Here the result is not impaired by rotational variations in the distance between the rotating retaining device and the measuring head since in this method it is the layer thicknesses which are determined, not the distances between the measuring head and the surface of the layers to be measured.

In a preferred embodiment the final thickness of the semiconductor wafer to be thinned is also entered in a coupling unit or control unit connected to the evaluation unit of the monitoring apparatus and a control unit of the wet etching apparatus. Finally in this embodiment the etching process is stopped when the predetermined final thickness for the thinned semiconductor wafer is reached.

In this method the final thickness is preferably entered, in particular down to a few hundred nanometers in stages of 10 nanometers, at the coupling unit or via a monitor with a touch screen. Instead of the touch screen it is also possible to use appropriately assigned function keys on a PC.

The semiconductor wafer can be fixed to the rotating retaining device, preferably with semiconductor wafers for final thicknesses of under 150 micrometers, by means of a substrate on which the semiconductor wafer to be thinned is fixed with an adhesive layer. As long as this adhesive layer is transparent to the light wave band of the light source, it is also possible to verify the thickness of the adhesive layer when thinning the semiconductor wafer.

To this end the semiconductor wafer to be thinned is first stuck to a substrate and the substrate is then fixed to the rotating semiconductor device by means of a vacuum or permanent magnet. Where the substrate is fixed to the retaining device by a permanent magnet said substrate contains a ferromagnetic material such cobalt, nickel, iron or alloys thereof.

With large final thicknesses, in particular, the semiconductor wafer can be fixed to the rotary table without a substrate by means of a vacuum.

In addition to the continuous detection of the thickness of the semiconductor wafer to be thinned, it is also possible to determine the thickness and evenness of an etching film consisting of the etching liquid applied and to regulate the quantity of etching liquid to be dispensed by a dispenser and/or the speed of rotation of the retaining device in accordance with the thickness measurement of the etching film. The relatively even thinning of the semiconductor wafer requires an even outflow and an even inflow of the etching solution, the buffer solution and/or the wetting agents. This can also be verified continuously using the evaluation unit and sent via the coupling unit on the appropriate signal lines to a regulator for the composition of the etching liquid and the speed of the motor of the rotating retaining device. Here the quantity and/or the composition of etching liquid to be applied can be regulated continuously during etching in accordance with the reduction in thickness of the semiconductor wafer.

In the embodiment which relates to the 1D-se FD-OCT and 1D-te FD-OCT methods, the spectrometer fans out the reflected beam spectrally. The spectral distribution of the reflected beam can be fanned out by means of a diffraction grating and a downstream diode line. In a further embodiment the wave lengths of the reflected beam measured are inverted and sent to the spectrometer for the aforementioned FD-OCT method.

An etching solution consisting of fluoric acid and an oxidising agent such as nitric acid, dissolved peroxydisulfate or dissolved Ce(IV) salts is applied to the surface of the semiconductor wafer to be thinned via the dispenser as an etching liquid for silicon wafers. Sulphuric acid and/or phosphoric acid can be added to buffer the etching rate and a liquid wetting agent can be admixed to improve wetting.

The measuring process can start after the etching process as the thickness measurement is an absolute measurement and the measuring process can therefore start shortly before the final thickness is achieved and there is still time for the stopping point and thus the replacement of the etching solution by a rinsing solution to start. The rinsing process starts as soon as the evaluation unit signals that the final thickness has been reached. The rinsing process can be followed by spin drying. Finally, it is possible, as mentioned above, to re-measure exactly the distribution of the final thickness or whether the whole etched surface matches or exceeds the final thickness using an appropriate multiple axis positioning system.

The at least one semiconductor wafer can be a silicon wafer to be thinned. Furthermore, the at least one semiconductor wafer can be a wafer made of a III-V or II-VI semiconductor material to be thinned. In particular, the at least one semiconductor wafer can be a wafer made of one of the semiconductor materials GaAs, InP, GaInAs or InAs to be thinned.

The invention is explained in further detail below with reference to the attached drawings.

Figure 1:
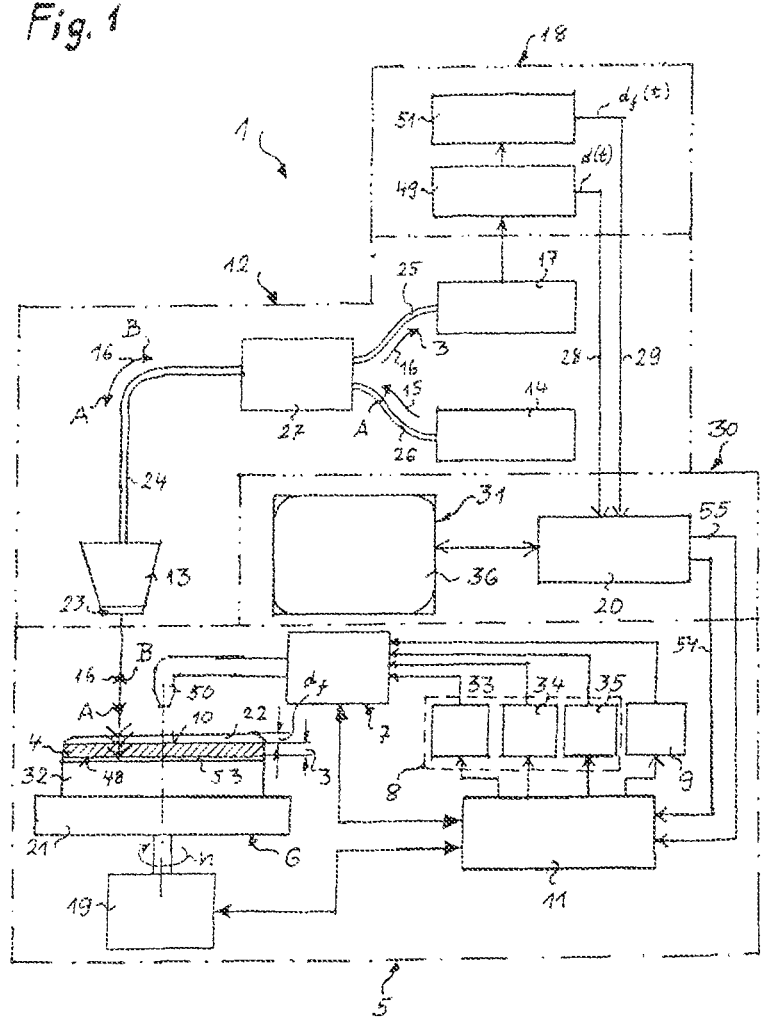
FIG. 1 shows a schematic structure for a thinning apparatus with a monitoring apparatus for the in-situ measurement of wafer thicknesses during the thinning of semiconductor wafers for monitoring the thinning of the semiconductor wafer in accordance with an one embodiment of the invention.
Figure 2:
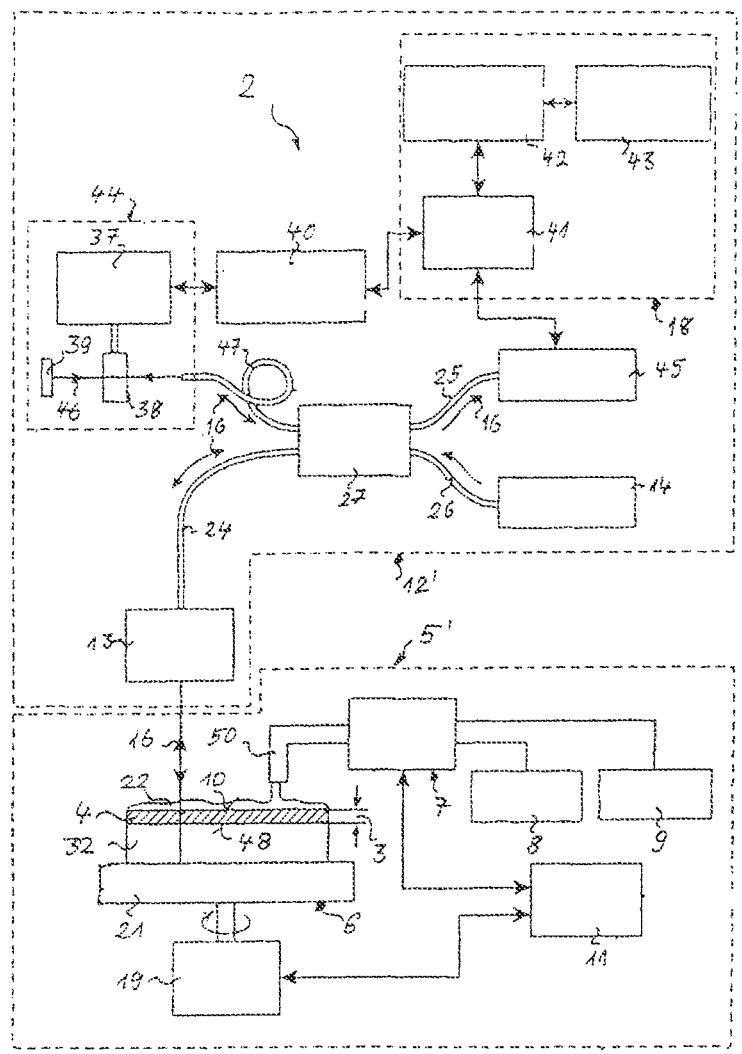
FIG. 2 shows a schematic structure for apparatus for measuring wafer thicknesses during the thinning of semiconductor wafers in accordance with the prior art.

FIG. 1 shows a schematic structure for a thinning apparatus 1 with a monitoring apparatus 12 for the in-situ measurement of wafer thicknesses 3 during the thinning of semiconductor wafers 4 for monitoring the thinning of the semiconductor wafer 4 in accordance with one embodiment of the invention. To this end, the thinning apparatus 1 essentially comprises two apparatuses, namely a wet etching apparatus 5 for thinning at least one semiconductor wafer 4 and the monitoring apparatus 12 for monitoring the thinning of the semiconductor wafer 4 and measuring the thickness 3 of the rotating semiconductor wafer 4 while it is being thinned. Positioned between the wet etching apparatus 5 and the monitoring apparatus 12 is a coupling unit 20 or an input and coupling unit 30 by means of which boundary and initial parameters, threshold values for light intensities and other parameters can be input and measuring results can be displayed.

The wet etching apparatus 5 for thinning at least one semiconductor wafer comprises a rotating retaining apparatus 6 for a semiconductor wafer 4 to be thinned. The wet etching apparatus 5 also has a dispenser 7 for etching liquids 8 and rinsing liquids 9 to be applied to a surface 10 of the rotating semiconductor wafer 4 to be thinned. Finally, the wet etching apparatus 5 has a control unit 11 for controlling the quantity of etching liquid 8 or rinsing liquid 9 to be applied and controlling the rotational speed n of the retaining device 6.

The second apparatus, namely the monitoring apparatus 12 for monitoring the thinning of the semiconductor wafer 4 and measuring the wafer thickness 3 of the rotating semiconductor wafer 4, has a measuring head 13 positioned contract-free at a distance from the surface 10 of the semiconductor wafer 4 to be etched. In this arrangement the accuracy of measurement of the wafer thickness 3 of the semiconductor wafer 4 is not impaired by the distance of the measuring head 13 from the surface 10 of the rotating semiconductor wafer 4. Moreover, the monitoring apparatus 12 has a light source 14 with coherent light emission 15 in the near-infrared range in a light wave band several tens of nanometers wide with which the measuring head 13 irradiates the semiconductor wafer 4 and receives the reflected beam 16. In the embodiment of the invention illustrated, the infrared range of the light wave band lies between 1.25 and 1.35 μm such that the measuring head 13 irradiates the semiconductor wafer 4 on the rotating retaining device 6 with a 100 nm wide light wave band contact-free in the direction of arrow A and the reflected beam is directed to a spectrometer 17 in the direction of arrow B.

The measuring head 13 is protected from the etching liquids 8 applied to the surface 10 of the semiconductor wafer 4 by means of a nozzle 50 of the dispenser 7 by an infrared-transparent protective screen 23 made of sapphire. The material of the protective screen 23 is crystalline, optically transparent $Al_2O_3$ and, as such, insensitive to the etching solutions used for a silicon semiconductor wafer. The measuring head 13 is connected via a first optical light wave guide 24 to a beam splitter, which is an optical coupler 27 in the embodiment shown, that is a component of the monitoring apparatus 12, it being possible for this optical light wave guide 24 to be several meters long such that the electronic circuitry of the measuring apparatus can be positioned at a distance from the robust measuring head and the aggressive wet etching apparatus 5 for thinning the semiconductor wafer. This electronic circuitry can also be provided in a separate measuring room.

The optical coupler 27 connects the infrared light source 14 of the near-infrared to the measuring head 13 via the first optical light wave guide 24 and a second light wave guide 26, a coherent light emission 15 being sent to the measuring head 13 via the second light wave guide 26, the optical coupler 27 and the first light wave guide 24. The reflected beam 16 is directed to a spectrometer 17 via the optical coupler 27 and a third light wave guide 25 in the direction of arrow B.

The spectrometer 17 fans out the reflected beam 16 spectrally after inversion of the reflected light wave lengths and directs the spectrum measured to the evaluation unit 18 to determine the wafer thickness. The evaluation unit 18 has two measuring blocks. In the embodiment shown a first measuring block 49 determines the wafer thickness d(t) by means of an FD-OCT method and delivers the value determined via a signal line 28 to the coupling unit 20. In the embodiment shown a second measuring block 51 determines the thickness $d_f(t)$ of the etching film at a given point in time by means of an FD-OCT method and continuously supplies the result determined to the coupling unit 20 via the signal line 29. Instead of a plurality of signal lines, it is also possible to provide a multiplex line.

The coupling unit 20 belongs to an input and coupling unit 30 which also operates as a control unit and can have a two-dimensional LC display, such as a monitor 31, which in this embodiment of the invention is fitted with a touch screen 36 such that it cannot only display measurement results but can also be used to input boundary and initial parameters using the touch screen 36 and appropriate input masks. The coupling unit 20 connects the evaluation unit 18 to the control unit 11 of the wet etching apparatus 5 for thinning the semiconductor wafer 4. Furthermore, the control unit 11 is connected to a dispenser 7 via a plurality of blocks 33 to 35 to form an etching liquid 8 and to a block for the rinsing liquid 9.

In this arrangement, an etching solution in the block 33 comprises two solution components for a silicon wafer, for example, consisting of fluoric acid and an oxidising agent such as nitric acid, dissolved peroxydisulfate or dissolved Ce(IV) salts. A wetting agent can be added in block 34 and a buffer solution consisting of sulphuric acid and/or phosphoric acid is prepared and fed to the dispenser 7 in block 35. In this arrangement, the compositions and mixing ratios can be adjusted to the semiconductor substrate material, the examples of solutions given above being appropriate for thinning a silicon wafer.

Since these solvents are highly transparent yet have refractive indexes different to the refractive indexes of the semiconductor wafer and the ambient air it is also possible to measure the thickness $d_f(t)$ of an etching film 22 which forms on the rotating semiconductor wafer 4 and determine it in the evaluation unit 18 such that the control unit 11 not only controls the rotational speed n of a motor 19 of the rotating retaining device 6 but also defines the composition and the individual quantities of the etching liquid 8 to be mixed in the dispenser 7 and dispensed via the nozzle 50. The rinsing liquid 9 is not used until the semiconductor wafer 4 to be thinned reaches its predetermined final thickness $d_Z$ and the etching process has to be stopped.

The semiconductor wafer 4 can be fixed to the rotary table 21 of the rotating retaining device 6 by various different methods. In this embodiment of the invention the semiconductor wafer 4 is fixed to a ferromagnetic substrate 32 using an adhesive layer 53, the rotary table 21 having a permanent magnet which fixes the ferromagnetic substrate 32 to the rotary table 21. In another embodiment of the invention, the rotating device 6 may also have a vacuum rotary table 21 which fixes an appropriate substrate 32 to the rotary table by means of a vacuum. A substrate of this type is used when final thicknesses below 150 micrometers need to be achieved. For larger final thicknesses the semiconductor wafer 4 can be fixed to the rotary table 21 by a vacuum.

The adhesive layer 53 preferably contains a thermoplastic so that, after thinning, when the substrate 32 has heated up slightly the semiconductor wafer 4 can be pressed down off the substrate 32, the semiconductor wafer 4 often being pushed with the substrate 32 in a direction of separation in order firstly to separate the thinned semiconductor wafer 4 into individual, thinned chips and then to detach the individual chips from the substrate 32. Since adhesive layers 53 of this type are also transparent, it is also possible to measure and verify the thickness of the adhesive layer 53 using the measuring apparatus 12 before, after or during etch thinning.

As both the boundary layer between the etching film 22 and the surface 10 of the semiconductor wafer 4 and the boundary layer between the adhesive layer and the surface 48 of the semiconductor wafer 4 can be determined using the spectrometric fanning out of the spectrum of the beam 16, this apparatus 1 is used to detect a plurality of layers. In this arrangement the constantly decreasing wafer thickness 3, i.e. the value d(t) measured in the evaluation unit 18, and the thickness d (t) of the etching film 22 are important for the thinning of the semiconductor wafer 4.

The thickness $d_f(t)$ of the etching film 22 can be changed using the rotational speed n of the drive motor 19 of the rotary tables 21, while the quantity and/or the composition of the etching liquid 8 can be adjusted/regulated using the three blocks 33 to 35 and the control unit 11 mentioned above. In this embodiment of the invention, the nozzle 50 is directed centrally towards the centre of the semiconductor wafer 4 or may be pivoted horizontally over the semiconductor wafer 4. This thinning apparatus 1 can also thin one single semiconductor wafer.

However, it is also possible to position a plurality of semiconductor wafers 4 in the edge regions of an enlarged rotary plate 21, while the nozzle 50 of the dispenser 7 is directed centrally towards the centre of the rotary table 21. In this arrangement it is advantageous if the substrate 32 covers the entire surface of the rotary table 21 and the individual semiconductor wafers to be thinned are fixed in the edge region of the common substrate 22 such that the etching liquid flows evenly over the wafer.

The input and coupling unit 30 can either be integrated in the wet etching apparatus 5 for thinning the semiconductor wafer 4 or be part of the monitoring apparatus 12. In addition, it is also possible to integrate the input and coupling unit 30, which is connected to both the evaluation unit 18 and the control unit 11 by signal lines 28, 29 and 54, 55 only, in a central monitoring room remote from the wet etching apparatus 5 and the monitoring apparatus 12. This shows that the arrangement of the individual components in the thinning apparatus 1 disclosed in the invention is extremely flexible, only the robust measuring head 13 having to be positioned a distance from the surface 10 of the semiconductor wafer 4 to be etched.

LIST OF REFERENCE NUMERALS

1 Thinning apparatus (embodiment of the invention)
2 Apparatus (prior art)
3 Wafer thickness
4 Semiconductor wafer
5 Wet etching apparatus
5' Apparatus
6 Rotating retaining device
7 Dispenser
8 Etching fluid
9 Rinsing liquid
10 Surface of the rotating semiconductor wafer
11 Control unit
12 Monitoring apparatus
12' Measuring apparatus
13 Measuring head
14 Light source
15 Light emission
16 Reflected beam
17 Spectrometer
18 Evaluation unit
19 Motor
20 Coupling unit
21 Rotary table
22 Etching film
23 Protective screen of the measuring head
24 Light wave guide (from and to the measuring head)
25 Light wave guide
26 Light wave guide
27 Optical coupler
28 Signal line
29 Signal line
30 Input and coupling unit
31 Monitor
32 Substrate
33 Block for etching solution
34 Wetting agent
35 Buffer solution
36 Touch screen
37 Galvanometer (mirror galvanometer)
38 Pivoting glass substrate
39 Reflector mirror
40 Optical image length detection
41 Signal processing circuit
42 Raw thickness calculation
43 Statistical thickness calculation
44 Reference light generator
45 Photo detector
46 Optical reference path
47 Optical reference light wave guide
48 Surface of the semiconductor wafer positioned on the retaining device
49 First measuring block
50 Dispenser nozzle
51 Second measuring block
53 Adhesive layer
54 Signal line
55 Signal line
d(t) Wafer thickness at a given point in time
Δd(t) Reduction in thickness of semiconductor wafer
$d_f(t)$ Etching film thickness at a given point in time
$d_z$ Final thickness of semiconductor wafer
λ Wave length of light beam
n Rotational speed

The invention claimed is:

1. A monitoring apparatus for monitoring the thinning of at least one semiconductor wafer in a wet etching apparatus, said monitoring apparatus comprising:

a light source configured to emit coherent light in a light wave band to which the semiconductor wafer is optically transparent;

a measuring head positioned contact-free in relation to a surface of the semiconductor wafer to be etched, the measuring head being configured to irradiate the semiconductor wafer with the coherent light of the light wave band and to receive a reflected beam reflected by the semiconductor wafer;

a spectrometer, the wavelengths ($\lambda$) of the reflected beam being inverted and fed to the spectrometer;

a beam splitter by which the coherent light of the light wave band is directed at the measuring head and the reflected beam is directed at the spectrometer; and an evaluation unit, said evaluation unit being configured to determine the thickness d(t) of the semiconductor wafer from the beam reflected by the semiconductor wafer during the thinning of the semiconductor wafer by a method selected from a group consisting of a 1D-se FD-OCT method, a 1D-te FD-OCT method, and a 1D-se TD-OCT method.

2. The monitoring apparatus according to claim 1, wherein the spectrometer includes a diffraction grating, said diffraction grating being configured to fan out the spectral distribution of the reflected beam.

3. The monitoring apparatus according to claim 1, wherein the measuring head includes an optically transparent protective screen.

4. The monitoring apparatus according to claim 1, wherein the evaluation unit is also configured to determine the thickness ($d_f(t)$) and the evenness of an etching film including of etching liquid.

5. The monitoring apparatus according to claim 1, wherein the beam splitter is an optical coupler.

6. The monitoring apparatus according to claim 5, wherein at least one first light wave guide connects the measuring head to the optical coupler, at least one second light wave guide connects the optical coupler to the light source, and at least one third light wave guide connects the optical coupler to the spectrometer.

7. A thinning apparatus comprising
a wet etching apparatus, and
a monitoring apparatus including:
  a light source configured to emit coherent light in a light wave band to which the semiconductor wafer is optically transparent;
  a measuring head positioned contact-free in relation to a surface of the semiconductor wafer to be etched, the measuring head being configured to irradiate the semiconductor wafer with the coherent light of the light wave band and to receive a beam reflected by the semiconductor wafer;
  a spectrometer;
  a beam splitter by which the coherent light of the light wave band is directed at the measuring head and the reflected beam is directed at the spectrometer;
  an evaluation unit, said evaluation unit being configured to determine the thickness d(t) of the semiconductor wafer from the beam reflected by the semiconductor wafer during the thinning of the semiconductor wafer by a method selected from a group consisting of a 1D-se FD-OCT method, a 1D-te FD-OCT method, and a 1D-se TD-OCT method;
  wherein the quantity and/or the composition of an etching liquid is adjusted continuously according to the reduction in thickness ($\Delta d(t)$) of the semiconductor wafer during etching.

8. The thinning apparatus according to claim 7, wherein the wet etching apparatus includes at least one rotating retaining apparatus for the semiconductor wafer to be thinned.

9. The thinning apparatus according to claim 7, wherein the thinning apparatus includes a coupling unit and a control unit of the wet etching apparatus, said coupling unit being connected to the evaluation unit and the control unit and configured to stop the etching process when the thinned semiconductor wafer reaches a predetermined final thickness ($d_z$).

10. The thinning apparatus according claim 7, wherein the etching liquid for a silicon wafer to be thinned contains an etching solution comprising fluoric acid and an oxidising agent and a buffer solution for buffering the etching process.

11. A method for monitoring the thinning of at least one optically transparent semiconductor wafer in a wet etching apparatus with a monitoring apparatus, said wet etching apparatus including at least one rotating retaining device and said method comprising the following steps:
  fixing at least one semiconductor wafer on the rotating retaining device;
  starting a measuring process by the activation of a light source and the emission of coherent light in a light wave band to which the semiconductor wafer is transparent, a measuring head irradiating the rotating semiconductor wafer with the coherent light of the light wave band and receiving a reflected beam, and by the activation of a spectrometer which receives the reflected beam, the wave lengths ($\lambda$) of the reflected beam being inverted and fed to the spectrometer;
  starting an etching process for thinning the rotating semiconductor wafer by the application of an etching liquid by means of a dispenser;
  evaluating the spectrometrically fanned out reflected beam to determine the thickness d(t) of the semiconductor wafer achieved during the thinning of the semiconductor wafer by means of a method selected from a group consisting of a 1D-se FD-OCT method, a 1D-te FD-OCT method and a 1D-se TD-OCT method.

12. The method according to claim 11, further comprising the following steps:
  inputting a final thickness ($d_z$) for the semiconductor wafer to be thinned at a coupling unit connected to an evaluation unit of the monitoring apparatus and a control unit of the wet etching apparatus;
  stopping the etching process when the predetermined final thickness (dz) for the thinned semiconductor wafer is achieved.

13. The method according to claim 11, wherein the semiconductor wafer is fixed to the rotating retaining device by means of a substrate and an adhesive layer.

14. The method according to claim 11, wherein the semiconductor wafer is fixed to the rotating retaining device by a vacuum.

15. The method according to claim 11, wherein, in addition to the thickness (d(t)) of the semiconductor wafer to be thinned, the thickness ($d_f(t)$) and the evenness of an etching film comprising etching liquid are also determined and the quantity per unit of time of etching liquid to be dispensed by the dispenser and the speed of rotation (n) of the retaining device is regulated according to the thickness measurement of the etching film.

16. The method according to claim 11, wherein the quantity and/or the composition of the etching liquid is adjusted continuously according to the reduction in thickness ($\Delta d(t)$) of the semiconductor wafer during etching.

17. The method according to claim 11, wherein the start of the measuring process takes place after the start of the etching process.

18. The method according to claim 11, wherein a rinsing process is started to stop the etching process and that the rinsing process is followed by spin drying.

19. The method according to claim 11, wherein the at least one semiconductor wafer is a silicon wafer to be thinned.

20. A method for monitoring the thinning of at least one optically transparent semiconductor wafer in a wet etching apparatus with a monitoring apparatus, said wet etching apparatus including at least one rotating retaining device and said method comprising the following steps:

fixing at least one semiconductor wafer on the rotating retaining device;

starting a measuring process by the activation of a light source and the emission of coherent light in a light wave band to which the semiconductor wafer is transparent, a measuring head irradiating the rotating semiconductor wafer with the coherent light of the light wave band and receiving a reflected beam, and by the activation of a spectrometer which receives the reflected beam;

starting an etching process for thinning the rotating semiconductor wafer by the application of an etching liquid by means of a dispenser;

evaluating the spectrometrically fanned out reflected beam to determine the thickness $d(t)$ of the semiconductor wafer achieved during the thinning of the semiconductor wafer by means of a method selected from a group consisting of a 1D-se FD-OCT method, a 1D-te FD-OCT method and a 1D-se TD-OCT method;

wherein the quantity and/or the composition of the etching liquid is adjusted continuously according to the reduction in thickness ($\Delta d(t)$) of the semiconductor wafer during etching.

* * * * *